United States Patent [19]

Hyatt et al.

[11] 4,374,770
[45] Feb. 22, 1983

[54] PROCESS FOR PREPARATION OF AROMATIC ACID CHLORIDES

[75] Inventors: John A. Hyatt; David S. Kashdan, both of Kingsport, Tenn.

[73] Assignee: Eastman Kodak Company, Rochester, N.Y.

[21] Appl. No.: 309,664

[22] Filed: Oct. 8, 1981

[51] Int. Cl.³ .................... C07C 107/06; C07C 51/58
[52] U.S. Cl. ........................... 260/207.1; 260/544 D; 260/465 D; 260/544 S; 560/77
[58] Field of Search .......... 260/544 D, 207.1, 465 D, 260/544 S; 560/77

[56] References Cited

U.S. PATENT DOCUMENTS 2,700,679 1/1955 Carnahan et al. ............. 260/544 M
3,962,326 6/1976 Semler et al. ................. 260/544 K
4,173,580 11/1979 Hemprecht .................... 260/543 R

OTHER PUBLICATIONS

Durrens, T. H., J. Chem. Society (London), (1922), pp. 44–49.
Patai, Saul, "The Chemistry of Acyl Halides", (1972), pp. 43–44.
Blankenhorn, Ernst, *Berichte der Duetschen Chemischen Gesellschaft*, (1877), pp. 441–445.

Primary Examiner—Natalie Trousof
Assistant Examiner—L. Hendriksen
Attorney, Agent, or Firm—Gary C. Bailey; J. Frederick Thomsen; Daniel B. Reece, III

[57] ABSTRACT

Disclosed is a process for converting aromatic aldehydes to the corresponding acid chlorides by reacting an aromatic aldehyde with sulfuryl chloride in the presence of a catalytic amount of a phosphine, phosphine oxide or phosphonium compound. The product compounds produced by the process of this invention are useful as chemical synthesis intermediates in the preparation of pharmaceuticals, dyes, herbicides and photographic chemicals.

20 Claims, No Drawings

PROCESS FOR PREPARATION OF AROMATIC ACID CHLORIDES

This invention relates to a process for the preparation of acid chlorides. More specifically, this invention concerns a process for making aromatic acid chlorides from aromatic aldehyde compounds.

Various methods for making aromatic acid chlorides from the corresponding aromatic aldehydes are known. In an early process [see Journal of the Chem. Soc. 121, 44 (1922)] benzaldehyde is reacted with a large excess of sulfuryl chloride, 1:5 molar ratio, to produce benzoyl chloride. Appreciable quantities of benzaldehyde are reported to be present. No yields are stated.

By another process reported in Chem. Abstract 82 155692, Netherlands patent application Ser. No. 73 06,212, benzoyl chloride is prepared by the reaction of benzaldehyde with chlorine in the presence of a radical generator, i.e., 0.1–5% peroxide and/or ultraviolet light.

Also reported in the literature is the reaction of aromatic aldehydes with carbon tetrahalides to give the corresponding acid chloride, see for example Zhur. Obscheikhim 34, 3473 (1964). This report states that benzoyl chloride is obtained in high yield by reacting carbon tetrachloride with benzaldehyde. This method has the undesirable feature, however, of requiring high reaction temperatures (160°–205° C.).

Still in some processes, special handling precautions are required for certain reactants. Reported in the Journal of Amer. Chem. Soc. 73, 702 (1951), is the reaction of benzaldehyde with t-butyl hypochlorite in carbon tetrachloride. The use of t-butyl hypochlorite is highly hazardous (violent decomposition occurs upon exposure to light, heat or rubber, −10° C. flash point). In a similar reaction, an aromatic aldehyde is reacted with chlorine in the presence of DMF (N,N-dimethylformamide) and sulfur chloride. Because of the toxicity of DMF, sulfur chloride, and chlorine caution must be exercised. The use of chlorine is inconvenient since it is more difficult to measure than other chlorinating agents such as sulfuryl chloride. (See Chem. Abstract 81 120238c, USSR Pat. No. 438,641, 1974).

By the process of our invention, aromatic aldehydes are converted to the corresponding acid chlorides rapidly and selectively and without the use of high reaction temperatures, unstable radical generators or special handling precautions found with the prior art processes. Moreover, our process can be conducted employing a wide variety of substituents on the aromatic ring without competing reactions occurring at the substituents.

According to the process of our invention aromatic acid chlorides having the formula

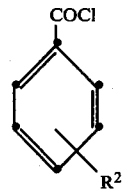

are prepared by reacting an aromatic aldehyde having the formula

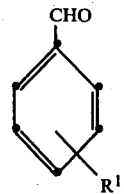

with sulfuryl chloride in the presence of a catalytic amount of a compound having the formula

In the above formulae $R^1$ is selected from the group consisting of hydrogen, alkyl of up to 8 carbon atoms, —($C_6H_4$)—$CH_3$, —CHO, and Z, wherein Z is an electron withdrawing group selected from the group consisting of —CN, —COCl, —$SO_2(C_6H_5)$, —$SO(C_6H_5)$, —N=N—$C_6H_5$ and —$CO_2R^7$ wherein $R^7$ is alkyl of up to 8 carbon atoms; $R^2$ is selected from the group consisting of hydrogen, alkyl of up to 8 carbon atoms, —($C_6H_4$)—$CH_3$, —COCl and Z; Y is selected from the group consisting of P, P=O and

wherein X is selected from the group consisting of chlorine and bromine; $R^8$ is selected from the group consisting of chlorine, bromine and M; and M, $R^4$, $R^5$ and $R^6$ are independently selected from the group consisting of alkyl and haloalkyl containing up to 8 carbon atoms and

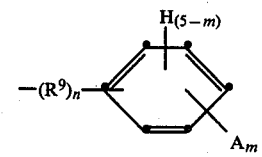

wherein $R^9$ is an alkylene group containing up to 8 carbon atoms, n is an integer from 0 to 1; A is selected from the group consisting of chlorine, bromine and alkyl and haloalkyl containing up to 8 carbon atoms, and m is an integer from 0 to 5.

We have found that by reacting aromatic aldehydes, as shown by formula II above (hereinafter referred to as aldehyde) with sulfuryl chloride in the presence of a catalytic amount of a phosphine, phosphine oxide or phosphonium compound, as shown by formula III above, (hereinafter referred to as phosphine compound), aromatic acid chlorides are favored, as shown by formula I above.

According to the process of our invention the concentration of phosphine compound can be as low as about 0.1 mol percent based on the amount of aldehyde. At lower concentrations the reaction proceeds at an undesirably slow rate and the amount of ring chlorinated by-products increases significantly. While limitations at the upper range will generally be dictated by economy and convenience, there is generally no advantage in conducting the reaction process in the presence of more than about 5 mol percent of phosphine compound. Therefore, the concentration is desirably about 0.1 to about 5 mol percent based on the aldehyde, with about 0.5 to about 2 mol percent being preferred.

Exemplary phosphine compounds which may be employed in the present reaction process are trimethylphosphine, trimethylphosphine oxide, trimethylphosphine dichloride, trimethylphosphine dibromide, tetramethylphosphonium chloride, ethyldimethylphosphine, diethylmethylphosphine, triethylphosphine, triethylphosphine oxide, butyldimethylphosphine, butyldimethylphosphine oxide, trioctylphosphine, trioctylphosphine dichloride, trioctylphosphine oxide, triphenylphosphine, triphenylphosphine oxide, triphenylphosphine dichloride, benzyltriphenylphosphonium chloride, methyltriphenylphosphonium chloride, diphenyltolylphosphine oxide, benzyldiphenylphosphine oxide, benzylidiphenylphosphine, dibenzylphenylphosphine, dibenzylphenylphosphine oxide, tri-p-tolylphosphine, tri-p-tolylphosphine oxide, (o-bromophenyl) diphenylphosphine, (o-chlorophenyl) diphenylphosphine, tris(p-chlorophenyl) phosphine oxide, (dibromomethyl) triphenylphosphonium bromide and the like.

The phosphine compounds generally preferred are the triarylphosphines and triarylphosphine oxides, with triphenylphosphine and triphenylphosphine oxide being most preferred. These compounds are generally lower in cost, which allows for a more economical process; they are nonpyrophoric and less volatile and afford a more convenient and safer process.

The starting materials for use in the present invention (i.e., sulfuryl chloride and aromatic aldehydes of the type previously described) are generally available commercially from a number of sources.

Since the reaction is essentially quantitative, the amount of sulfuryl chloride will ordinarily be at least one mole equivalent per mole equivalent of formyl group. To enhance the rate of conversion and to ensure complete reaction at each formyl group, an excess of sulfuryl chloride is desirable, up to about 50% excess per mole equivalent of formyl group normally being sufficient, with about 10 to 20% excess per mole equivalent being preferred. Amounts beyond this will generally risk increasing the amount of ring chlorinated contaminants which in turn decreases the yield of acid chloride product.

The aromatic aldehydes which are suitable for the process of our invention are generally known in the art. Typical of these compounds are benzaldehyde, tolualdehyde (o—, m— and p—), carbomethoxybenzaldehyde (o—, m— and p—) and the like.

The process of the present invention is especially convenient since a solvent is not required. However, if desired, the reaction can be conducted in a solvent. Suitable for our process are unreactive organic solvents such as chlorobenzene, orthodichlorobenzene, 1,2,4-trichlorobenzene, dichloroethane, tetrachloroethylene and the like. The amount of solvent is primarily dictated by economic considerations such as the cost of the solvent, ease and expense of recovery and the efficient use of equipment. Generally, a solvent to reactant ratio of about 1–10:1 is satisfactory, with a ratio of about 1–4:1 being preferred.

The reaction conditions for our process are conventional for acid chloride processes. The reaction conveniently is carried out at atmospheric pressure, under an oxygen-free atmosphere. The temperature of reaction will normally be between about 25° C. to reflux (about 130° C. in the case of chlorobenzene) and preferably between about 60° C. to about 100° C. At temperatures below 25° C. the reaction rate slows drastically. At the preferred temperature range of about 60° C. to about 100° C. conversion proceeds rapidly with the reaction being substantially complete within about 1.5 to 3 hours on a laboratory scale. The reaction proceeds in the dark as well as in the light. However, the rate of reaction decreases by a factor of about 2 when conducted in the dark.

Following completion of the reaction the solvent is evaporated from the crude reaction mixture and the pure product isolated by fractional distillation, crystallization or by other suitable conventional separation means. Modifications to these exemplary conditions which are appropriate to the process of the present invention are well within the expertise of those skilled in the art.

By the process of this invention, aromatic acid chlorides are obtained in good yields, in the case of p-carbomethoxybenzaldehyde up to 98% purity. The products produced by this process have uses widely known in the art. They are particularly useful as chemical synthesis intermediates in the preparation of widely used products such as pharmaceuticals, dyes, herbicides, photographic chemicals and the like.

The following examples are given to further illustrate the invention, but it is to be understood that the invention is not to be limited in any way by the details described therein.

EXAMPLE 1

This example illustrates the preparation of p-carbomethoxybenzoylchloride by the reaction of methyl p-formylbenzoate with sulfuryl chloride in the presence of triphenylphosphine.

A solution of 32.8 g (0.20 mole) of methyl p-formylbenzoate and 0.66 g (0.003 mole) of triphenylphosphine in 130 ml of chlorobenzene was purged with nitrogen for 20 min., heated to 90°–100° C., and treated dropwise over 1.5 hr. with a solution of 28.1 g (0.21 mole) of sulfuryl chloride in 20 ml of chlorobenzene. The colorless mixture was held at 90° for 30 min. after the addition was complete, and the chlorobenzene was removed by distillation *in vacuo*. The residue of 40.2 g white solid was shown by IR, NMR and VPC analysis to be p-carbomethoxybenzoyl chloride of >98% purity.

EXAMPLE 2

This example illustrates the preparation of p-toluyl chloride by the reaction of p-tolualdehyde with sulfuryl chloride in the presence of triphenylphosphine. A mixture of 12.0 g of p-tolualdehyde, 0.3 g of triphenylphosphine, and 30 ml of chlorobenzene was stirred at 90°–100° C. under $N_2$ atmosphere and treated dropwise with a total of 9.5 ml of sulfuryl chloride over one hour. The reaction mixture was then distilled *in vacuo* to afford 12.6 g (81.7% yield) of p-toluyl chloride, b.p. 60°–67° at 1.5 mm Hg.

EXAMPLE 3

This example illustrates the reaction of o-tolualdehyde with sulfuryl chloride in the presence of triphenylphosphine. A mixture of 12.0 g of o-tolualdehyde, 0.3 g of triphenyl phosphine, and 20 ml of chlorobenzene was stirred at 90° under an $N_2$ atmosphere. A total of 17 ml of sulfuryl chloride was added to this mixture over 2.0 hrs., after which distillation *in vacuo* yielded 11.4 g (74%) of pure o-toluyl chloride, bp 80°-83° C./4 mm Hg.

The invention has been described in detail with particular reference to certain preferred embodiments thereof, but it will be understood that variations and modifications can be effected within the spirit and scope of the invention.

We claim:

1. Process for preparation of a compound having the formula

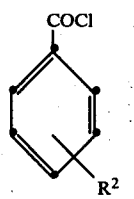

which comprises reacting an aromatic aldehyde having the formula

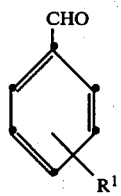

with sulfuryl chloride, wherein $R^1$ is selected from the group consisting of hydrogen and alkyl of up to 8 carbon atoms, —$(C_6H_4)$—$CH_3$, —CHO and Z, wherein Z is an electron withdrawing group selected from the group consisting of —CN, —COCl, —$SO_2(C_6H_5)$, —$SO(C_6H_5)$, —N=N—$C_6H_5$ and —$CO_2R^7$ wherein $R^7$ is alkyl of up to 8 carbon atoms; $R^2$ is selected from the group consisting of hydrogen, alkyl of up to 8 carbon atoms, —$(C_6H_4)$—$CH_3$, —COCl and Z; the reaction being conducted in the presence of a catalytic amount of a compound having the formula

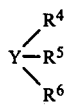

wherein Y is selected from the group consisting of P, P=O, and

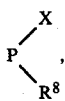

wherein X is selected from the group consisting of chlorine and bromine; $R^8$ is selected from the group consisting of chlorine, bromine and M; and M, $R^4$, $R^5$ and $R^6$ are independently selected from the group consisting of alkyl and haloalkyl

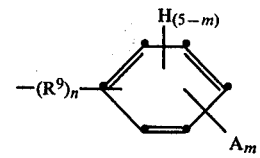

wherein $R^9$ is an alkylene group containing up to 8 carbon atoms, n is an integer from 0 to 1; A is selected from the group consisting of chlorine, bromine and alkyl and haloalkyl containing up to 8 carbon atoms, and m is an integer from 0 to 5.

2. Process according to claim 1 wherein the concentration of the compound

is about 0.1 to about 5 mol percent based on the aromatic aldehyde.

3. Process according to claim 2 wherein at least one mole equivalent of sulfuryl chloride is present per mole equivalent of formyl group.

4. Process according to claim 1 wherein the concentration of the compound

is about 0.5 mol percent to about 2 mol percent based on the aromatic aldehyde.

5. Process according to claim 4 wherein the mole equivalent ratio of sulfuryl chloride to formyl group is about 1-1.2:1.

6. Process according to claim 1 wherein the reaction is conducted in an unreactive organic solvent, the solvent to reactant ratio being about 1-10:1.

7. Process according to claim 6 wherein the solvent is chlorobenzene.

8. Process according to claim 1 wherein the reaction is conducted at a temperature of from about 25° C. to reflux.

9. Process according to claim 1 wherein the reaction is conducted at a temperature of from about 60° C. to about 100° C.

10. Process according to claim 1 wherein the reaction is conducted in an oxygen free atmosphere.

11. Process for preparation of a compound having the formula

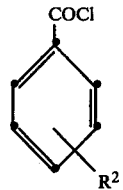

which comprises reacting an aromatic aldehyde having the formula

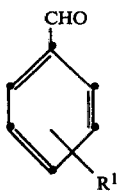

with sulfuryl chloride, wherein R$^1$ is selected from the group consisting of hydrogen and alkyl of up to 8 carbon atoms, —(C$_6$H$_4$)—CH$_3$, —CHO and Z, wherein Z is an electron withdrawing group selected from the group consisting of —CN, —COCl, —SO$_2$(C$_6$H$_5$), —SO(C$_6$H$_5$), —N═N—C$_6$H$_5$ and —CO$_2$R$^7$ wherein R$^7$ is alkyl of up to 8 carbon atoms; R$^2$ is selected from the group consisting of hydrogen, alkyl of up to 8 carbon atoms, —(C$_6$H$_4$)—CH$_3$, —COCl and Z; the reaction being conducted in the presence of a catalytic amount of triphenylphosphine or triphenylphosphine oxide.

12. Process according to claim 11 wherein the concentration of triphenylphosphine or triphenylphosphine oxide is about 0.1 to about 5 mol percent based on the aromatic aldehyde.

13. Process according to claim 12 wherein at least one mole equivalent of sulfuryl chloride is present per mole equivalent of formyl group.

14. Process according to claim 11 wherein the concentration of triphenylphosphine or triphenylphosphine oxide is about 0.5 to about 2 mol percent based on the aromatic aldehyde.

15. Process according to claim 14 wherein the mole equivalent ratio of sulfuryl chloride to formyl group is about 1–1.2:1.

16. Process according to claim 11 wherein the reaction is conducted in an unreactive organic solvent, the solvent to reactant ratio being about 1–10:1.

17. Process according to claim 16 wherein the solvent is chlorobenzene.

18. Process according to claim 11 wherein the reaction is conducted at a temperature of from about 25° C. to reflux.

19. Process according to claim 11 wherein the reaction is conducted at a temperature of from about 60° C. to about 100° C.

20. Process according to claim 11 wherein the reaction is conducted in an oxygen free atmosphere.

* * * * *